(12) United States Patent
Xu et al.

(10) Patent No.: US 12,085,534 B2
(45) Date of Patent: Sep. 10, 2024

(54) MULTIPLEXABLE SUPER-RESOLUTION FORCE SPECTROSCOPY USING ULTRASOUND METHODS AND MAGNETIC DETECTION

(71) Applicant: University of Houston System, Houston, TX (US)

(72) Inventors: Shoujun Xu, Houston, TX (US); Yuhong Wang, Houston, TX (US); Haina Jia, Houston, TX (US); Heng Yin, Houston, TX (US); Yujia Mao, Houston, TX (US)

(73) Assignee: UNIVERSITY OF HOUSTON SYSTEM, Houston, TX (US)

( * ) Notice: Subject to any disclaimer, the term of this patent is extended or adjusted under 35 U.S.C. 154(b) by 1070 days.

(21) Appl. No.: 16/968,535

(22) PCT Filed: Feb. 6, 2019

(86) PCT No.: PCT/US2019/016822
§ 371 (c)(1),
(2) Date: Aug. 7, 2020

(87) PCT Pub. No.: WO2019/157038
PCT Pub. Date: Aug. 15, 2019

(65) Prior Publication Data
US 2021/0041395 A1 Feb. 11, 2021

Related U.S. Application Data
(60) Provisional application No. 62/628,188, filed on Feb. 8, 2018.

(51) Int. Cl.
*B06B 1/02* (2006.01)
*B06B 1/06* (2006.01)
(Continued)

(52) U.S. Cl.
CPC ........... *G01N 27/72* (2013.01); *B06B 1/0207* (2013.01); *B06B 1/0622* (2013.01);
(Continued)

(58) Field of Classification Search
CPC ...... G01N 27/72; G01N 33/15; B06B 1/0207; B06B 1/0662; B06B 1/0651; B06B 2201/77; G01R 33/1269; B01J 19/10
See application file for complete search history.

(56) References Cited

U.S. PATENT DOCUMENTS

| 4,074,070 A * | 2/1978 | Gaus ........................ H04R 3/00 381/99 |
| 2013/0104667 A1* | 5/2013 | Koyano .................. G01F 15/14 73/861.25 |

(Continued)

OTHER PUBLICATIONS

Viehmann, ("Magnetometer Based on the Hall Effect," The Review of Scientific Instruments, vol. 33, No. 5, May 1962) (Year: 1962).*

(Continued)

*Primary Examiner* — Jill A Warden
*Assistant Examiner* — Michael Stanley Gzybowski
(74) *Attorney, Agent, or Firm* — CONLEY ROSE, P.C.

(57) ABSTRACT

A method of measuring dissociation of the biomolecular bonds in one or multiple sample wells using super-resolution force spectroscopy (SURFS). SURFS utilizes precise ultrasound radiation to exert an acoustic radiation force on the biomolecular bonds labeled with magnetic particles. The force-induced dissociation of the protein bonds labeled with magnetic particles may be measured as a reduced magnetic signal by a magnetic sensor. The force resolution allows for differentiating biomolecular bonds with an extremely high level of precision. The biomolecular bonds include protein- (Continued)

protein, protein-nucleic acid, nucleic acid-nucleic acid, small molecule-protein, and small molecule-nucleic acid interactions.

20 Claims, 7 Drawing Sheets

Specification includes a Sequence Listing.

(51) Int. Cl.
  *G01N 27/72* (2006.01)
  *G01N 33/15* (2006.01)
(52) U.S. Cl.
  CPC ............ *B06B 1/0651* (2013.01); *G01N 33/15* (2013.01); *B06B 2201/77* (2013.01)

(56) References Cited

U.S. PATENT DOCUMENTS

2013/0139575 A1\* 6/2013 Lee .................. G01N 29/04
  73/61.75

2015/0117156 A1\* 4/2015 Xu ..................... G01R 33/1269
  367/137

OTHER PUBLICATIONS

International Patent Application No. PCT/US2019/016822 International Search Report and Written Opinion dated Jul. 1, 2019 (23 pages).

Sitters, Gerrit et al., "Acoustic force spectroscopy," Nature Methods, Jan. 2015, vol. 12, No. 1, pp. 47-50 and its legend (7 pages).

Yao, Li et al., "Noninvasive Measurement of the Mechanical Force Generated by Motor Protein EF-G during Ribosome Translocation," Angewandte Chemie International Edition, Dec. 23, 2013, vol. 52, pp. 14041-14044 and its Supporting Information (16 pages).

Qui, Yongqiang et al., "Acoustic Devices for Particle and Cell Manipulation and Sensing," Sensors 2014, vol. 14, pp. 14806-14838 (33 pages).

Xu, Shoujun, "A High-Resolution High-Efficiency Force Spectroscopy for Measuring Drug-DNA Interactions," Award Abstract # 1508845, Jul. 1, 2015, https://www.nsf.gov/awardsearch/showAward?AWD_ID=1508845>; Retrieved on May 27, 2019 (4 pages).

\* cited by examiner

SEQUENCE LISTING

```
<160> NUMBER OF SEQ ID NOS: 1

<210> SEQ ID NO 1
<211> LENGTH: 11
<212> TYPE: DNA
<213> ORGANISM: Artificial
<220> FEATURE:
<223> OTHER INFORMATION: 11-base-pair-DNA

<400> SEQUENCE: 1
ccaatcgacc c                                                        11
```

MULTIPLEXABLE SUPER-RESOLUTION FORCE SPECTROSCOPY USING ULTRASOUND METHODS AND MAGNETIC DETECTION

CROSS-REFERENCE TO RELATED APPLICATIONS

The present application is a National Phase Entry of, and claims priority to PCT Application No. PCT/US2019/016822, filed Feb. 6, 2019, which claims priority to U.S. Provisional Patent Application No. 62/628,188, filed Feb. 8, 2018, entitled "Multiplexable Super-Resolution Force Spectroscopy Using Ultrasound Methods and Magnetic Detection," the entire contents of each being hereby incorporated herein by reference in their entirety for all purposes.

STATEMENT REGARDING FEDERALLY SPONSORED RESEARCH OR DEVELOPMENT

This invention was made with government support under R01 GM111452 awarded by the National Institutes of Health, and 1508845 awarded by the National Science Foundation. The government has certain rights in the invention.

FIELD OF THE INVENTION

The present disclosure relates to the fields of multiplexable super-resolution force spectroscopy that may in some embodiments resolve intermolecular bonds, reveal molecular motion, and distinguish multiple-step protein binding.

BACKGROUND

Many force spectroscopy techniques have been developed and widely used in fundamental biological research. Examples are atomic force microscopy, AFM (Florin, et al., Science 264, 415-417 (1994); Wong, et al., Nature 394, 52-55 (1998)); Bai et al., Biochem. Biophys. Res. Commun. 448, 372-378 (2014)) optical tweezers OT (Bustamante, et al., Nature 421, 423-427 (2003); Ota, et al., Appl. Phys. Lett. 87, 043901 (2005)); acoustic force spectroscopy, AFS (Sitters, et al., Nat. Method 12, 47-50 (2015)); magnetic tweezers (Strick, et al., Science 271, 1835-1837 (1996)); and force-induced remnant magnetization spectroscopy, FIRMS (Yao, et al., Angew. Chem. Int. Ed. 50, 4407-4409 (2011); Yao, et al., J. Phys. Chem. B 116, 9944-9948 (2012); De Silva, et al., J. Phys. Chem. B 117, 7554-7558 (2013)).

The majority of these techniques are single-molecule based and use optical detection. Consequently, they have several drawbacks.

The first is poor force resolution. For example, a typical force histogram by AFM is 20-40 pN wide. Although different force histograms have been obtained to indicate different binding sites or protein interactions, they have substantial overlap and are difficult to quantify (Pfreundschuh, et al., Nat. Commun. 6:8857/doi: 10.1038/ncomms9857 (2015)). Better force resolution is thus highly desired.

The second is the poor efficiency. The force traces are usually obtained one by one for the single-molecule techniques. This approach makes it very difficult to find specific ligand-receptor bonds because these bonds only represent in a small percentage (~8-10%) among all specific and non-specific interactions on the surface. It is therefore not surprising that some studies contained a significant part of weaker, nonspecific interactions (Hu, et al., Chem. Commun. 52, 3705-3708 (2016); Dobrowsky, et. al., J. Virol. 82, 7022-7033 (2008).

In addition, for AFM, the stiffness of the cantilevers and force history often lead to inconsistent results.

While FIRMS achieves a 1.8 pN force resolution, enabling differentiation of DNA duplexes with one nucleotide difference, and recently ultrasound has been used to achieve similar force resolution. Such experimental state of the art applications are capable of distinguishing for example: the binding and non-binding of drugs with DNA based on differential binding forces, and the ribosome motion on the mRNA during translocation and frameshifting (De Silva, et al., L., Chem. Comm. 50, 10786-10789 (2014); Hu, et al., Angew. Chem. Int. Ed. 53, 14135-14138 (2014); Tsai, et al., ACS Chem. Biol. 12, 1629-1635 (2017).

However, such force resolution is not sufficient to quantify drug-DNA binding to sub-pN precision, or reveal molecular motion beyond one nucleotide length, and the approach of using a commercial ultrasound probe makes it difficult to automate the overall FIRMS device. Therefore, there is an unmet need in the field, and it is necessary to develop new experimental techniques to study such systems (Walton, et al., Biophys. J. 94, 2621-2630 (2008); Pincet, et al., Biophys. J. 89, 4374-4381 (2005)).

BRIEF SUMMARY OF THE DISCLOSED EMBODIMENTS

Multiplexable super-resolution force spectroscopy (SURFS) as disclosed herein aims to address an unmet need in the field, wherein the methods disclosed provide for resolution of intermolecular bonds, revealing molecular motion, and distinguishing multiple-step protein binding, by providing a method of highly refined force resolution.

The present disclosure relates in some embodiments to a method of measuring the dissociation of protein bonds using super-resolution force spectroscopy (SURFS). SURFS utilizes precise ultrasound radiation to exert an acoustic radiation force on protein bonds labelled with magnetic particles; the force-induced dissociation of the protein bonds labelled with magnetic particles may be measured as a reduced magnetic signal by a magnetic sensor, such as an atomic magnetometer, giant magnetoresistive sensor, hall probe, or superconducting quantum interference One embodiment disclosed herein is drawn to a super resolution force spectroscopic (SURFS) apparatus configured to measure the dissociation of molecular bonds, said apparatus comprising at least one piezo plate; a compartment comprising liquid, wherein the compartment is positioned above the piezo plate; a sample-plate, placed above the compartment; a magnetic sensor; and transport apparatus configured to move the sample-plate between a first location, and a second location, wherein the sensor measures the changes in magnetism proportional to bond dissociation. In some embodiments the apparatus further comprises a function generator, in some embodiments the apparatus also comprises an amplifier, wherein in some embodiments, the amplifier is radiofrequency amplifier, in other embodiments the amplifier is an ac (alternating current) amplifier. In some other embodiments of the apparatus the first location is at the piezo plate, in other embodiments the second location is at the magnetic sensor. In some embodiments of the apparatus the transport apparatus is a motor or multiple motors. In some embodiments of the apparatus described herein the piezo plate is about 1 mm-100 mm in width, in some embodiment the piezo plate is about 1 mm-100 mm in length, and in other embodiments the piezo plate is about 0.3-10 mm in thickness. In some embodiments the first location and the second location overlap.

In some embodiments the apparatus herein described, further comprises a function generator, wherein the functional generator and an amplifier generate an amplified alternating current, in another embodiment the alternating current has a frequency of between 20 kHz and 5 MHz, and in a further embodiment the alternating current has an amplitude of between about 0.01 V and about 20 V. In some embodiments of the apparatus of the maximum power of the radiofrequency amplifier is 10-1000 watts. In another embodiment of the apparatus, the magnetic sensor is an atomic magnetometer, a superconducting quantum interference device, a Hall probe, or a magnetoresistive-based sensor. In a further embodiment of the apparatus, the sample plate comprises 1 to 10,000 sample wells. In another embodiment of the apparatus the piezo plates are in the range of 1-1000, and in a further embodiment the piezo plates are in the range of 1-10.

Another embodiment herein discloses a super resolution force spectroscopic (SURFS) apparatus configured for generating an acoustic force and measuring bond dissociation in multiple samples simultaneously, wherein the apparatus comprising: at least one piezo plate, wherein the plate is driven by an amplified ultrasound radiation; a layer of grease positioned on a first surface of the piezo plate; a sample plate comprising at least one sample well, wherein the piezo plate generates an acoustic force onto each said sample well; a magnetic sensor; a transport apparatus configured to move the sample plate between a first location, and a second location; wherein said sensor measures the changes in magnetism proportional to bond dissociation for the multiple samples. In one embodiment of the apparatus, the at least one piezo plate is in the range of about 1-1000. In another embodiment of the apparatus, the layer of grease is positioned between the sample and piezo plate, in a further embodiment the grease is a commercial vacuum grease, wherein said grease in one embodiment is a lubricant with low volatility, and in a still further embodiment the thickness of the layer of grease is 0.001-0.5 mm. in some embodiments the grease is a lubricant, and in some further embodiments a layer of lubricant is in liquid form positioned between the sample and the piezo plate, with thickness of about 0.001-5 mm.

In another embodiment an apparatus configured for producing multiple acoustic forces within a single application of ultrasound is disclosed, wherein the apparatus comprises an array of piezo plates, wherein each plate is coupled in series with a capacitor, wherein said capacitor adjusts voltage; a sample, positioned within a sample-plate at each said piezo plate; a motor; and a single magnetic sensor or an array of magnetic sensors for detection. In another embodiment of the apparatus, the array of piezo elements is configured as a one dimensional array, in another embodiment the one dimensional array is a straight line or curve. In a further embodiment the array of piezo elements is configured as a two dimensional array, and in a still further embodiment the two dimensional array are multiple lines and patterns. In some embodiments of the apparatus the capacitors comprise a range of capacitances, wherein said values of capacitances are obtained by calculation and adjusted experimentally, and in another embodiment the motor is one of a linear motor for a one-dimensional scan, or two orthogonal motors for two-dimensional scan.

In another embodiment a method of measuring bond dissociation with super resolution force spectroscopy (SURFS), is disclosed, method comprising: (a) transporting a sample-plate comprising at least one sample to a first location, wherein said first location comprises a magnetic sensor, and measuring a first magnetic signal; (b) transporting said sample plate to a second location, wherein said second location comprises a piezo plate, and applying a first amplitude of ultrasound radiation, (c) transporting the sample plate to said first location and measuring a second magnetic signal; (d) transporting said sample plate to said second location, and applying a second amplitude of ultrasound radiation, wherein said second amplitude of ultrasound radiation is greater than said first amplitude of ultrasound radiation; and (e) Calculating the difference between the first magnetic signal, and said second magnetic signal, (f) repeating steps a-e until a statistically significant difference is measured, wherein the difference between the first and the second magnetic signal is proportional to the force required to dissociate molecular bonds of said sample. In some embodiments of the method transporting further comprises a motor. In other embodiments of the method herein disclosed the sample comprises biomolecules, wherein said biomolecules are labeled with magnetic particles, and the biomolecules are nucleic acids, proteins, ribosome complexes, receptors on cell surfaces, or combinations thereof.

The force resolution may be in the order of about 0.5 pN, which is approximately one order of magnitude better than the force spectroscopy techniques of the prior art, wherein for example, the associated spatial resolution for molecular motion is about 0.2 nm, which cannot be revealed by structural techniques such as X-ray crystallography and cryo-electron microscopy. In some embodiments, with a range of differential force fields, time resolution of about 1-3 min may be achieved, allowing the resolution of the multiple steps of protein binding.

The concept of multiplexed force spectroscopy with gradient forces has not been realized in force spectroscopy applications of the prior art. It is therefore disclosed herein that generating different forces within a single force application enables efficient data acquisition of force spectra. It also implements time resolution to resolve multiple steps of ligand-receptor binding, which is common in in vivo biological and biochemical processes, for example, during the fusion of a HIV virus.

Further, it is disclosed herein, that in some embodiments the force resolution can be correlated to high spatial resolution for molecular motion. By measuring the binding force between a probe DNA and a targeted molecular system the dimensional information of the system can be extracted. For example, in some embodiments it can be shown that the ribosome-mRNA complex has a very subtle motion of 0.2 nm from the post-translocation state to the subsequent pre-translocation state.

In another embodiment, the SURFS technique may be used to precisely resolve protein bonds on living cells. Compared to other force spectroscopic techniques, primarily atomic force microscopy (AFM) and optical tweezers, the force resolution method disclosed herein is about fifty times more accurate as compared to single-molecule techniques which typically provide a force distribution of 20-40 pN. Therefore, the methods disclosed herein may be applicable to revealing different protein bonds on living cell surface and identifying the influence of drug molecules.

BRIEF DESCRIPTION OF THE DRAWINGS

For a detailed description of the disclosed embodiments, reference will now be made to the accompanying drawings, wherein:

FIG. 5 depicts an embodiment of SURFS used to probe molecular motion in ribosome translocation, wherein (a) provides a depiction of an embodiment of the probing scheme, in which a magnetically labelled DNA (bottom) is used to form duplexes with various ribosome-mRNA complexes, shown as Post(MFEK) and Pre(MFEKR), while panel (b) depicts a force spectra for the two DNA-ribosome structures depicted in a.

DETAILED DESCRIPTION OF DISCLOSED EXEMPLARY EMBODIMENTS

Figure 1:
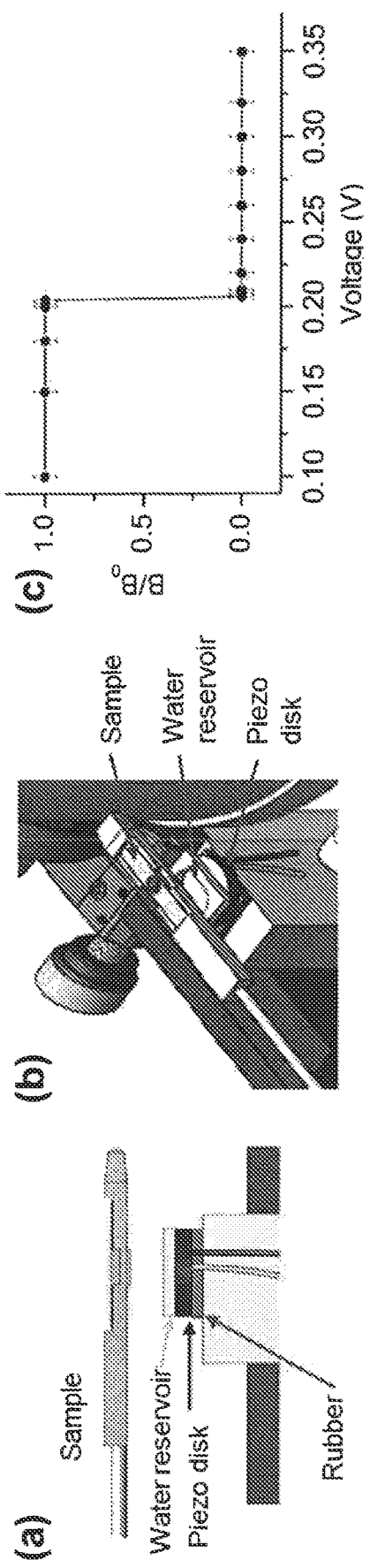
FIG. 1 depicts an embodiment of the SURFS technique described herein, where (a) depicts the precise control of ultrasound radiation to the sample; and (b) depicts a technical drawing of an embodiment of the apparatus setup; and (c) depicts a force spectrum of 12-bp DNA duplex, with a sequence of CCCAAT CGA CCC.

The following description is directed to various exemplary embodiments of the invention. However, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and that the scope of this disclosure, including the claims, is not limited to that embodiment.

Certain terms are used throughout the following description, and claims to refer to particular features or components. As one skilled in the art will appreciate, different persons may refer to the same feature or component by different names. This document does not intend to distinguish between components or features that differ in name but not function. The drawing figures are not necessarily to scale. Certain features and components herein may be shown exaggerated in scale or in somewhat schematic form, and some details of conventional elements may be omitted in interest of clarity and conciseness. In the following discussion and in the claims, the terms "including" and "comprising" are used in an open-ended fashion, and thus should be interpreted to mean "including, but not limited to . . . .". As used herein, the term "about," when used in conjunction with a percentage or other numerical amount, means plus or minus 10% of that percentage or other numerical amount. For example, the term "about 80%," would encompass 80% plus or minus 8%. References cited herein are incorporated in their entirety. Also, the term "couple" or "coupled" is intended to mean either an indirect or direct electrical connection. Thus, if a first device is coupled to a second device, that connection may be through a direct electrical connection of the two devices, or through an indirect electrical connection, established via other intermediate devices and connections.

Figure 3:
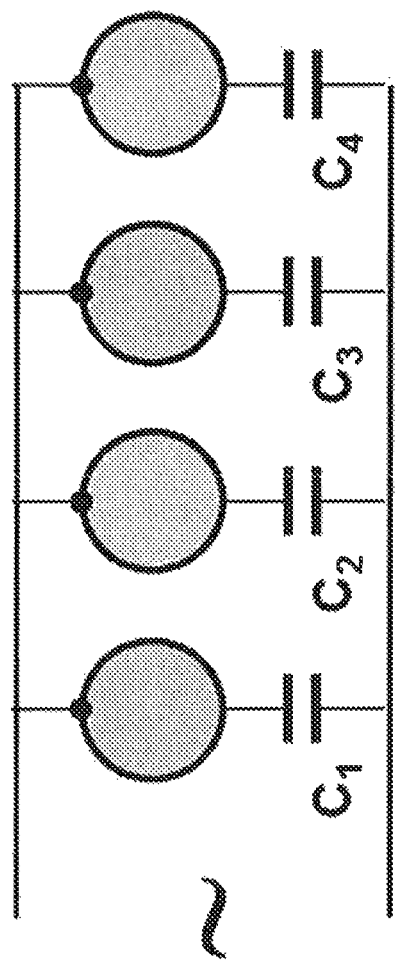
FIG. 3 depicts a graphic representation of an embodiment of a circuit to produce different forces at different piezo plates (the use of piezo elements and piezo plates in the context of this application are interchangeable) indicated as a circle by varying the capacitors $C_1$-$C_4$ as voltage dividers in accordance with principles described herein.

Embodiments disclosed herein are intended to overcome certain above mentioned limitations by using SURFS, which provides for a number of advancements over the prior art as disclosed herein and throughout the disclosure. One such advancement is to use precisely controlled ultrasound as the force source. By using a water reservoir as the medium between the piezo disk or plate and the sample, a precise force field may be obtained, and the thermal effect is significantly reduced. A second advancement is to automate the associated apparatus such that the sample can be alternately scanned for magnetic measurement and fixed for force application in many cycles (see FIG. 3b). The ultrasound power was gradually increased after each cycle wherein the automation substantially reduced operational errors. This is achieved by incrementing the amplitude of the output of a function generator prior to amplification.

EXAMPLES

FIG. 1a shows the scheme of an embodiment of such a precise ultrasound control. A piezo plate was placed on a piece of rubber. On top of the piezo, a water reservoir was constructed. The sample was mounted on a glass rod for scanning. The bottom of the sample, which contains the immobilized molecular system, makes contact with the water surface prior to ultrasound application. The water level was carefully monitored to be constant during experiment. FIG. 1b shows the technical drawing of the sample, piezo, and water reservoir. A DNA duplex with 12-basepair (bp) was used to calculate the force resolution. The dissociation voltage was determined to be 0.204 V on the function generator, with ±0.001 V resolution. The dissociation force of the same 12-bp DNA was also measured using FIRMS, which was revealed to be 45 pN. Because the acoustic radiation force is proportional to the ultrasound power, or $V^2$, the force resolution can be calculated as $$\delta F = (2\delta V/V)*F = (2*0.001/0.204)*45 = 0.5 \text{ pN} \quad (1)$$

Here, F is the bond dissociation force, and V is the dissociation voltage for ultrasound. $\delta F$ and $\delta V$ represent resolution of F and V, respectively.

Multiplexed SURFS using a single piezo plate: To accommodate multiple samples, a larger piezo plate is used. Depending on the size of each sample well and the total number of sample wells needed, the typical in-plane dimension of the piezo plate may be 5-100 mm in various shapes, and the thickness is typically 0.2-10 mm. Various large piezo plates are commercially available, for example, from American Piezo Company, and can be easily cut into customized sizes. Larger piezo plates have larger capacitances than the smaller ones, which lead to lower applied voltages. The equation governing the maximum voltage (Vmax) is:

$$V\max = I\max/(2\pi f C) \quad (2)$$

Herein, Imax is the current rating of the amplifier, f is the frequency of sine ultrasound wave, and C is the capacitance. Because the acoustic force is proportional to the square of voltage, a high-current amplifier is required to drive a large piezo plate.

Figure 2:
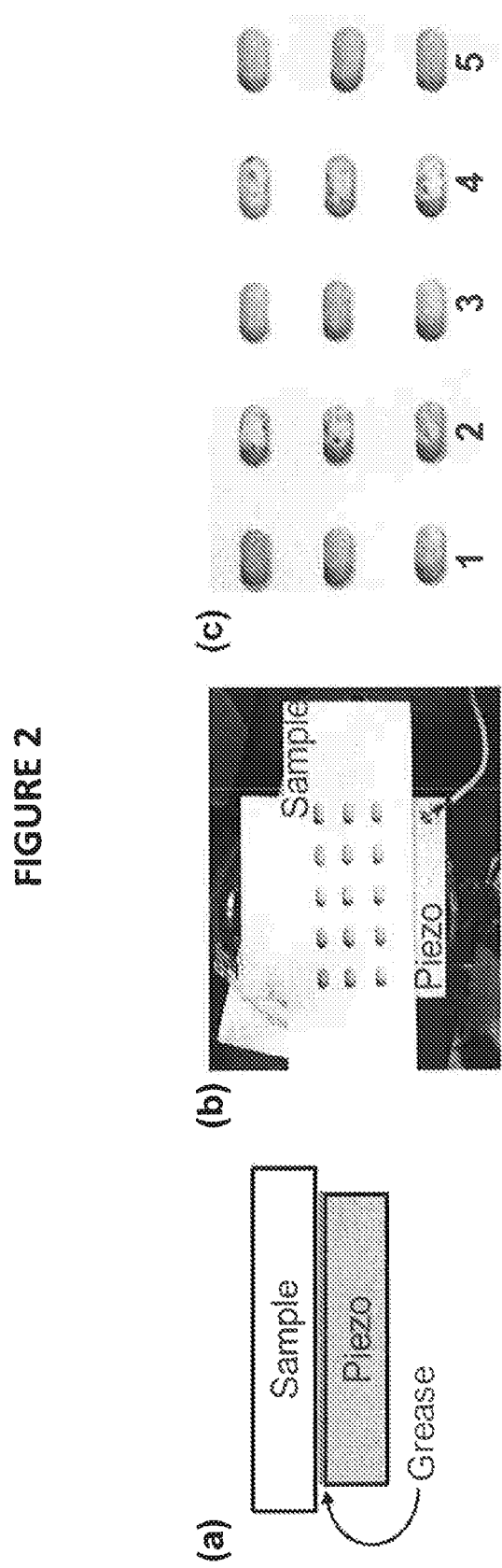
FIG. 2 depicts an embodiment of the multiplexed detection using a large piezo plate, wherein (a) depicts an embodiment of the setup, in which a 15-well sample was placed on the piezo plate and (b) depicts a sample prior to ultrasound application, while (c) is a depiction of the sample after sonication, wherein samples in rows 2 and 4 were visibly dissociated, while those in rows 1, 3, and 5 remained intact.

In addition to the scheme shown in FIG. 1a, another viable scheme is shown in FIG. 2a. Herein, in this embodiment a thin layer of grease may be applied on the piezo surface; then the sample plate containing multiple sample wells was placed on top of the piezo. Using a 40×40 mm² piezo (2 mm thick) as an example, the capacitance was measured to be 15.6 nF (FIG. 2b, bottom square). The resonance frequency is 1 MHz. In order to apply 8 V on the piezo (0.2 V prior to amplification), the current rating of the amplifier must to be greater than Imax, which will be in the current embodiment 0.78 A. The corresponding force will be approximately 45 pN based on the result in FIG. 1c. An amplifier 75A250A from AR (Souderton, PA, USA) was used in this embodiment.

The sample plate contained fifteen sample wells (FIG. 2b, top plate). The first, third, and fifth rows were specifically bound magnetic particles via DNA duplexes; the second and fourth rows were non-specifically bound magnetic particles. Therefore, at a small force, particle dissociation would be expected for Rows 2 and 4, but not for Rows 1, 3, and 5. The results are shown in FIG. 2c, in which only Rows 2 and 4 contained dissociated particles as expected. Thus, this embodiment disclosed that it is possible to use a large piezo plate to apply force on multiple samples.

Gradient force field using piezo plates coupled with voltage dividers: Prior to the current disclosure, the time resolution of force spectroscopy has been poor because the data points were acquired one at a time. For example, to obtain a force spectrum with 15 data points, 15 different forces are needed and magnetic measurement will follow each force application. Each data point will take about 3 minutes. Hence, the time resolution is on the order of one hour. This may not be sufficient to study multiple-step protein binding events, such as the sequential binding of gp120 onto CD4 receptor and CXCR4 co-receptor for example.

The time resolution of such measurements is advanced by embodiments of SURFS as disclosed herein, and is thus achieved by generating a gradient force field. Herein, in some embodiments an array of individual piezo plates may be used instead of a single one. The plates are in parallel, but each is coupled with a different capacitor in series. The capacitances of the capacitors ($C_1$-$C_4$ in FIG. 3) may be calculated based on voltage dividers. For example, if only half of the voltage needs to be applied on a particular piezo, the capacitor should have the same capacitance as the piezo. The resulting force will be one quarter of the force without the capacitor, denoted as $F_0$. In general, if the designated force is a factor of $\chi$ of $F_0$ and C represents the piezo capacitance, then the capacitance of the coupling capacitor will be given by:

$$C_i = (\sqrt{\chi} + 1)C \quad (3)$$

The gradient force field produced by adjusting the coupling capacitors may therefore improve the time resolution of SURFS. For example, in some embodiments the number of force applications may be reduced by 4 if four identical samples are used at different forces, which improves the force resolution by a factor of 4. By using more piezo elements in parallel, the whole force spectrum can be obtained within a single ultrasound application.

Applications of SURFS

With high force resolution, spatial resolution, and time resolution, SURFS may be utilized in biological research and biotechnology industrial branches, some such embodiments are disclosed herein.

Drug Molecules

Key questions in the design and development of drug molecules include the issue of how a drug interacts with their molecular target(s), including how effective is the drug for inhibiting the targeted ligand-receptor pair. Another is how the drug functions, i.e., whether it works through allosteric effect or directly blocks the ligand's binding pocket. Typically, binding affinity in concentration is used to characterize drug's efficacy. However, it does not provide information on the binding mechanism. Specifically, considering as an example CXCR4 and CCR5, both have been viable drug targets for HIV. A number of drug candidates have been developed, with one of them "Maraviroc" having been approved. X-ray structure showed that Maraviroc functions through allosteric effect that weakens the binding between gp120 and CCR5. However, it is unknown how much weaker the binding becomes and how effective it is on the cell surface.

SURFS, in some embodiments may be used to provide a precise differential binding force, $\Delta F$, to quantify the effect of drug molecules: wherein the presence of the drug altered the binding force of ligand-receptor bonds from F to F', so $\Delta F = F - F'$. [See U.S. Pat. No. 9,778,249 further incorporated herein in its entirety] Given that $\Delta F$ in some will be different for allosteric vs. direct blocking: $\Delta F$ will be smaller for allosteric effect than for direct blocking. Embodiments of the methods disclosed herein have showed that $\Delta F$ accurately revealed the chiral selectivity of drug molecules and sequence specificity of DNA duplexes. The values of $\Delta F$ were typically 5-16 pN. $\Delta F$ may have a greater range in such an embodiment because drug molecules usually have higher affinity for proteins than for DNAs.

Figure 4:
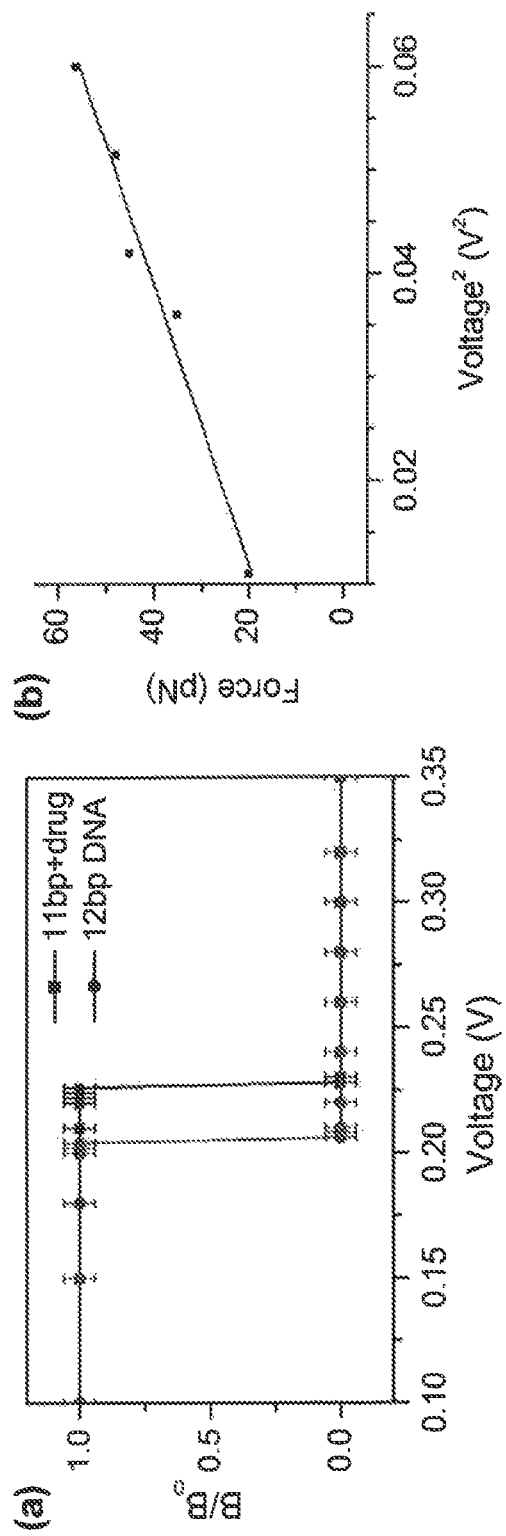
FIG. 4 depicts a graphical representation of resolving DNA-drug bonds from DNA duplexes, wherein (a) depicts resolving two close binding forces, 12-bp DNA and drug-bound 11-bp DNA. 11-bp DNA: ds(CCAAT CGA CCC); drug: daunomycin, and (b) depicts the calibration of force vs. the square of voltages, $V^2$, in accordance with principles described herein.

FIG. 4 shows the advantage of the high force resolution methods disclosed herein for resolving drug interactions. In FIG. 4a, the force spectra of 12-bp DNA and daunomycin bound 11-bp DNA are compared. The two dissociation voltages were well distinguished, with the former at 0.204 V and the latter at 0.226 V. However, previous techniques of the prior art cannot distinguish the two forces, which are 45±2 and 48±2 pN respectively. In other words, it can now be concluded using the methods disclosed herein that daunomycin-11-bp DNA is stronger than 12-bp DNA.

Another embodiment of the SURFS method herein disclosed was used to measure a series of DNA and DNA-drug complexes, and correlated the dissociation voltages with forces obtained by FIRMS. Linear fitting produces:

$$F = 740V^2 + 11 \quad (4)$$

This equation confirms that the dissociation force linearly depends on the ultrasound power (represented by $V^2$).

Molecular Motion Revealed by SURFS

Ribosomal translocation is a key step in protein synthesis. For each translocation step, the ribosome moves by three nucleotides from the pre-translocation state (Pre-complex) to the post-translocation state (Post-complex). Then, the ribosome will be in the pre-translocation state for the next translocation cycle. No technique of the prior art has revealed any difference between the "Post-complex of the previous step" and the "Pre-complex of the next step". In other words, in light of the prior art it is unclear how the ribosome moves along the mRNA to decode genetic information.

However, embodiments are herein disclosed that comprise a probing scheme based on SURFS to precisely determine the position of the ribosome on the mRNA. Shown in FIG. 5a, a probe DNA labelled with magnetic particle to form duplexes with the exposed mRNA is disclosed. The number of base-pairs can be derived from the dissociation forces of the duplexes. Typically, one A-T nucleotide pairing will increase the force by 8-12 pN, and one C-G pairing will increase by 15-20 pN, after the minimum number of base pairing (~9-10) to form a stable duplex.

Figure 5:
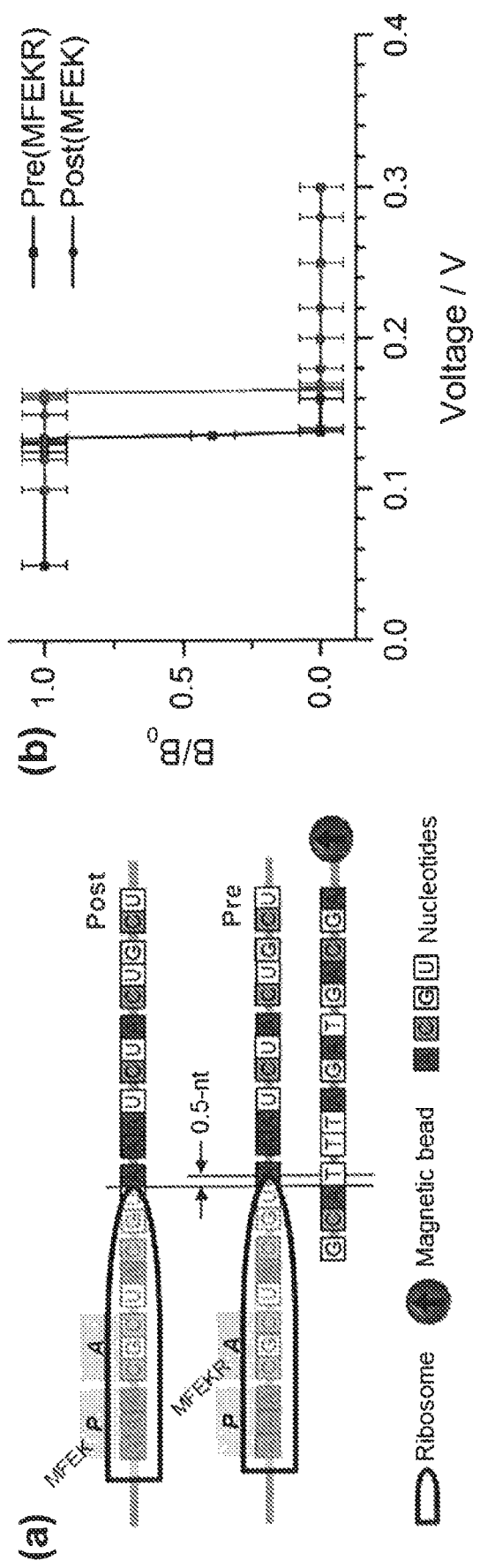

The force spectra in FIG. 5b reveal that the force difference is very small but detectable. The dissociation voltages differ by 0.03 V. Compared to the results in FIG. 4, the force difference is on the order of about 3-5 pN, much less than a complete basepair. This indicates there is a definite motion of the ribosome going from Post-complex step to the next Pre-complex step, but the motion is less than one nucleotide. Thus, such a step cannot be revealed by prior art methods, but is disclosed by the application of SURFS as described herein (because the space between neighbouring nucleotide is about 0.5 nm, the motion can be considered to be a fraction of this distance, or about 0.2 nm).

Resolving Multiple Binding Steps

Embodiments of the scheme of differential force field disclosed herein, enables the study of multiple-step binding, such as the infusion of the HIV infection. The most current prior art model for the infusion mechanism is that the viral envelope glycoprotein, gp120, first binds with the CD4 receptor on the cell surface and then with a co-receptor, CCR5 or CXCR4; fusion subsequently takes place between the virus and the cell. However, direct evidence for the molecular mechanism of this process remains elusive.

Figure 6:
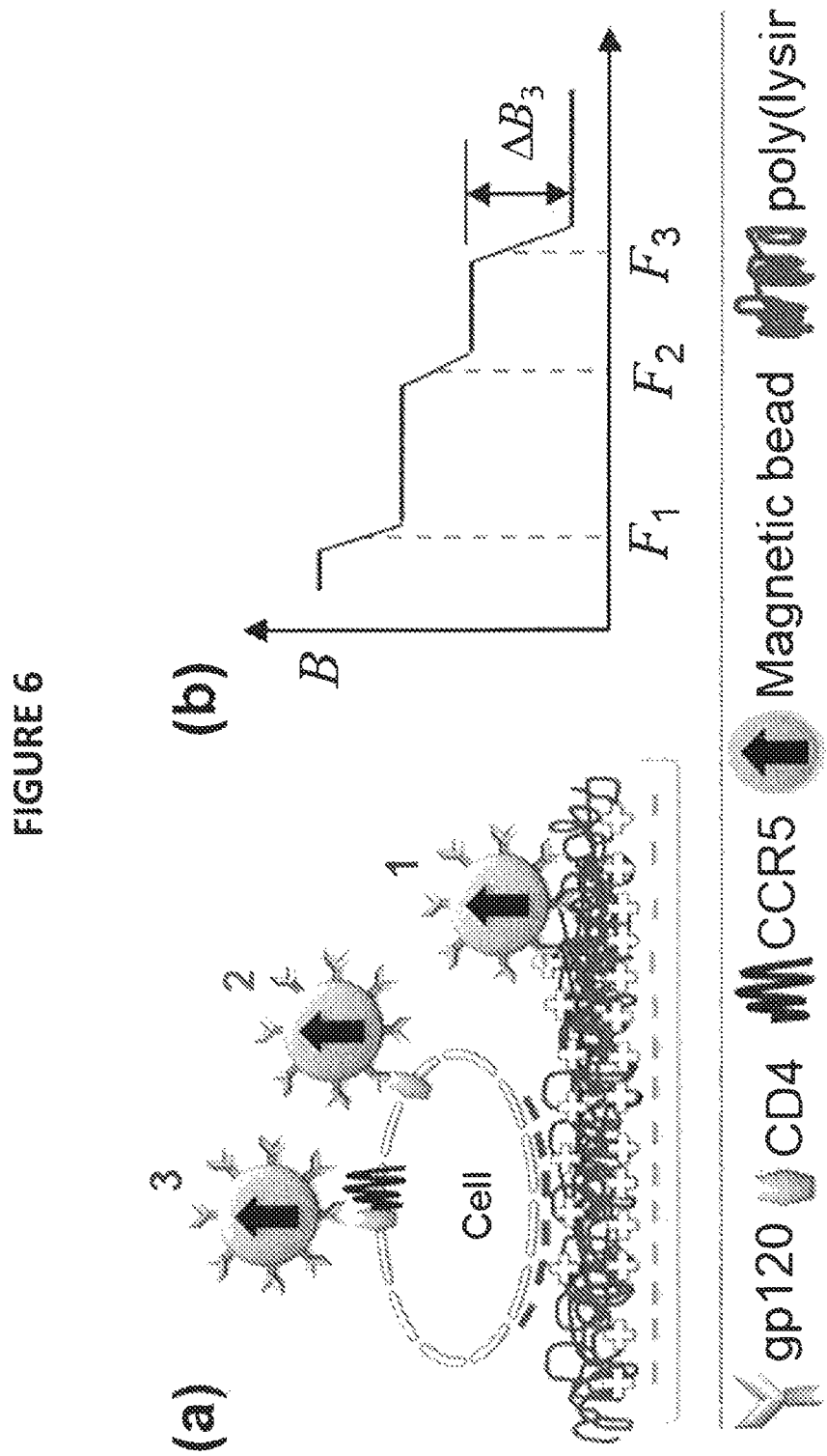
FIG. 6 depicts an illustration of using SURFS to resolve multiple binding steps, wherein panel (a) depicts a schematic of different binding, and panel (b) depicts a simulated force spectrum.
Figure 7:
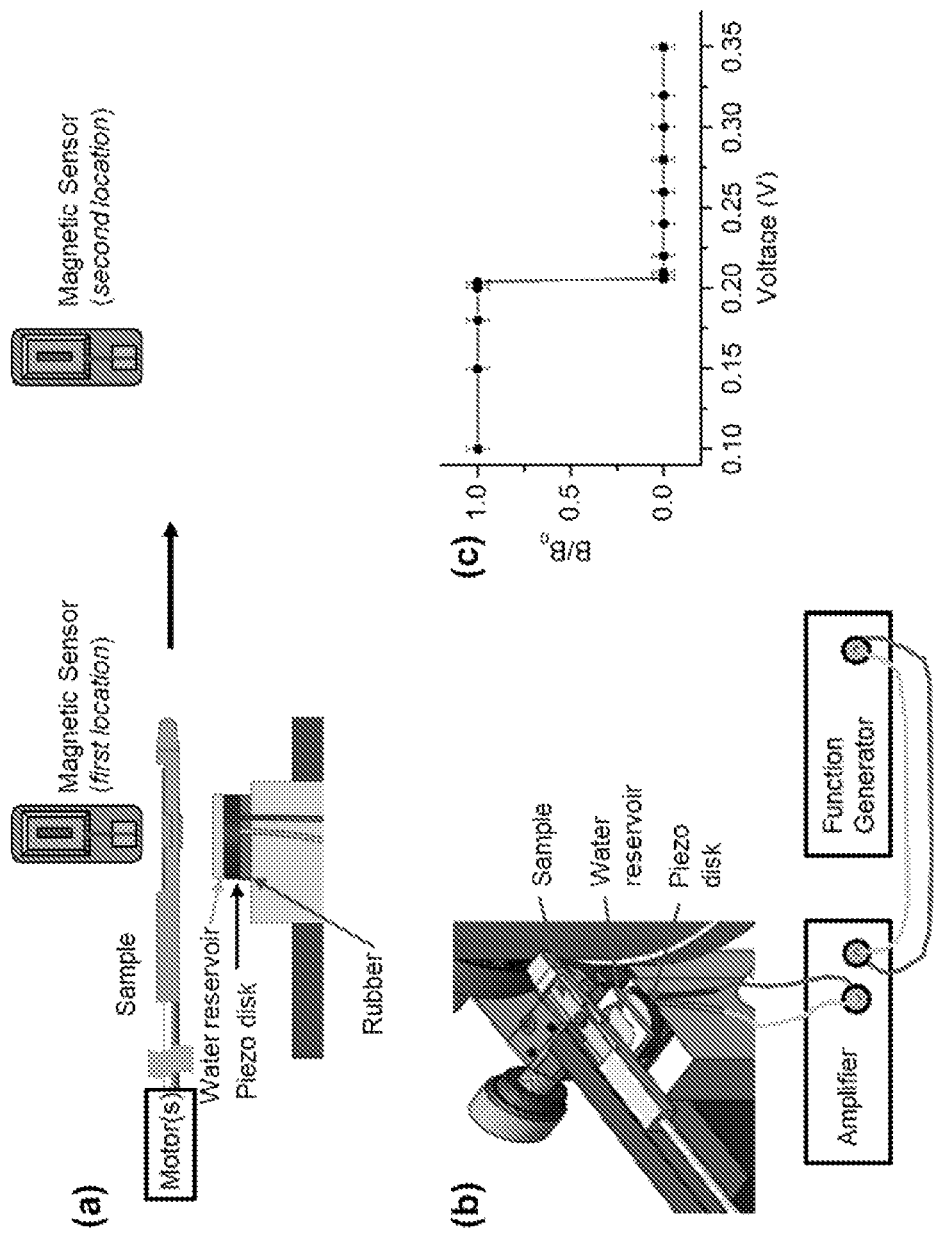
FIG. 7 depicts an further embodiment of the SURFS technique described herein, where (a) depicts the precise control of ultrasound radiation to the sample and indicates a first and second location for a magnetic senor; and (b) depicts a technical drawing of an embodiment of the apparatus setup and connectivity of an amplifier, and generator as described in embodiments herein; and (c) further depicts a force spectrum of 12-bp DNA duplex, with a sequence of CCCAAT CGA CCC.

SURFS with time resolution as disclosed herein is well suited to address the resolution of this mechanistic question. It has been shown that gp120 binds with CD4 fairly rapidly on the substrate surface, within 2-3 min, whereas the complete fusion between the HIV virus and the cells takes approximately 60 min. Therefore, both force resolution and time resolution should be used to resolve the two steps. Shown in FIG. 6, there will be three types of bonds: weak nonspecific bonds ($F_1$), strong gp120-CD4 bonds ($F_2$), and stronger gp120-CD4-CCR5/CXCR4 ($F_3$) bonds. At an earlier time (such as t1), the force spectrum should only show binding forces of $F_1$ and $F_2$, but not $F_3$. Gradually (t>t1) $F_3$ will appear in the force spectrum at longer reaction time, with amplitude designated as $\Delta B_3$. The binding kinetics between gp120 and the CCR5/CXCR4 co-receptor will thus be obtained by plotting $\Delta B^3$ vs. time t.

SURFS may also be employed in some embodiments to investigate drug molecules targeting the second binding step. The efficacy will be shown as two parameters, one is the differential binding force and the other is the second step binding amplitude, $\Delta B^3$.

Thus, disclosed herein is a multiplexable SURFS technique that addresses the unmet need for sub-pN force resolution for the binding forces of intermolecular bonds, 0.2 nm spatial resolution on molecular motion along nucleic acids, and ~2 min time resolution for multiple-step protein binding, capabilities of SURFS as disclosed herein may be extended to study protein binding on living cells.

What is claimed is:

1. An apparatus for measuring Apparatus to measure the dissociation of molecular bonds in an immobilized molecule said apparatus comprising:
   at least one piezo plate;
   grease or a compartment comprising a liquid, wherein the grease or the compartment is positioned on the piezo plate;
   a sample-plate containing one or more samples of the immobilized molecule, positioned above said grease or said compartment;
   a magnetic sensor;
   rubber, wherein the at least one piezo plate is positioned between the rubber and the grease or the compartment comprising the liquid; and
   transport apparatus configured to move the sample-plate between a first location, and a second location, wherein said magnetic sensor is configured to measure changes in magnetism proportional to bond dissociation of the molecular bonds.

2. The apparatus of claim 1, wherein the first location is at the at least one piezo plate.

3. The apparatus of claim 1, wherein the second location is at the magnetic sensor.

4. The apparatus of claim 1, wherein the transport apparatus comprises a motor or multiple motors.

5. The apparatus of claim 1, wherein the at least one piezo plate is about 1 mm-100 mm in width, about 1 mm-100 mm in length, and about 0.3 mm-10 mm in thickness.

6. The apparatus of claim 1, wherein the magnetic sensor is a superconducting quantum interference device, a Hall probe, or a magnetoresistive-based sensor.

7. The apparatus of claim 1, wherein said sample-plate comprises 1 to 10,000 sample wells.

8. The apparatus of claim 1, wherein a number of the at least one piezo plate is in the range of 1-1000.

9. The apparatus of claim 1, wherein the first location and the second location overlap.

10. The apparatus of claim 1, wherein a force resolution of the apparatus is sub piconewton (pN), and wherein a spatial resolution for molecular motion is less than or equal to about 0.2 nm and/or wherein a time resolution for measuring bond dissociation is in a range of from about 1 to about 3 min.

11. The apparatus of claim 1, wherein a bottom of the one or more samples contacts the grease or a liquid in the compartment prior to application of ultrasound radiation by the at least one piezo plate.

12. The apparatus of claim 1, further comprising a function generator configured to generate an alternating current, the function generator electrically connected to the at least one piezo plate.

13. The apparatus of claim 12, further comprising an amplifier electrically connected to the at least one piezo plate, wherein the amplifier is an ac (alternating current) amplifier.

14. The apparatus of claim 13, wherein the function generator, and the amplifier generate an amplified alternating current, wherein the amplified alternating current has a frequency of between 20 kHz and 5 MHz, and wherein the amplified alternating current has an amplitude of between 0.01 V and 20 V, and the amplified alternating current is applied to the at least one piezo plate.

15. The apparatus of claim 13, wherein a maximum power of the amplifier is 10-1000 watts.

16. An apparatus for generating an acoustic force and measuring bond dissociation in multiple samples of a molecule simultaneously, said apparatus comprising:
at least one piezo plate, wherein the at least one piezo plate is driven by an amplified ultrasound radiation;
a layer of a lubricant positioned on a first surface of said at least one piezo plate;
rubber in contact with a second surface of said at least one piezo plate;
a sample plate comprising at least one sample well, wherein the a piezo plate each of the at least one piezo plate is configured to generate an acoustic force onto each of the at least one sample well;
a magnetic sensor; and
transport apparatus configured to move the sample plate between a first location, and a second location;
wherein said magnetic sensor is configured to measure the changes in magnetism that are proportional to bond dissociation of the multiple samples.

17. The apparatus of claim 16, wherein a number of the at least one piezo plate is in the range of 1-1000.

18. The apparatus of claim 16, wherein the layer of lubricant is a vacuum grease positioned between the multiple samples and the at least one piezo plate, and wherein a thickness of the layer of vacuum grease is about 0.001-0.5 mm.

19. The apparatus of claim 16, wherein the layer of lubricant is liquid positioned between the multiple samples and the at least one piezo plate, wherein said layer of liquid has a thickness of about 0.001 mm-5 mm.

20. The apparatus of claim 16, wherein the first location and the second location overlap.

* * * * *